US00PP36937P2

(12) United States Plant Patent
Barshaw

(10) Patent No.: US PP36,937 P2
(45) Date of Patent: Sep. 2, 2025

(54) ***COREOPSIS* PLANT NAMED 'Baluptold'**

(50) Latin Name: *Coreopsis hybrida*
Varietal Denomination: Baluptold

(71) Applicant: Ball Horticultural Company, West Chicago, IL (US)

(72) Inventor: Darren Barshaw, Grand Haven, MI (US)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 0 days.

(21) Appl. No.: 18/914,143

(22) Filed: Oct. 12, 2024

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./263.1, 417
See application file for complete search history.

(56) References Cited

U.S. PATENT DOCUMENTS

PP28,865 P2 * 1/2018 Winner ..... Plt./417

* cited by examiner

*Primary Examiner* — Karen M Redden
(74) *Attorney, Agent, or Firm* — C. Anne Whealy

(57) ABSTRACT

A new and distinct cultivar of *Coreopsis* plant named 'Baluptold', characterized by its upright and mounded plant habit; moderately vigorous growth habit; freely branching habit; medium green-colored leaves; freely flowering habit with numerous inflorescences per plant; single-type daisy inflorescences with bright yellow-colored ray florets; and good garden performance.

2 Drawing Sheets

Figure 1:
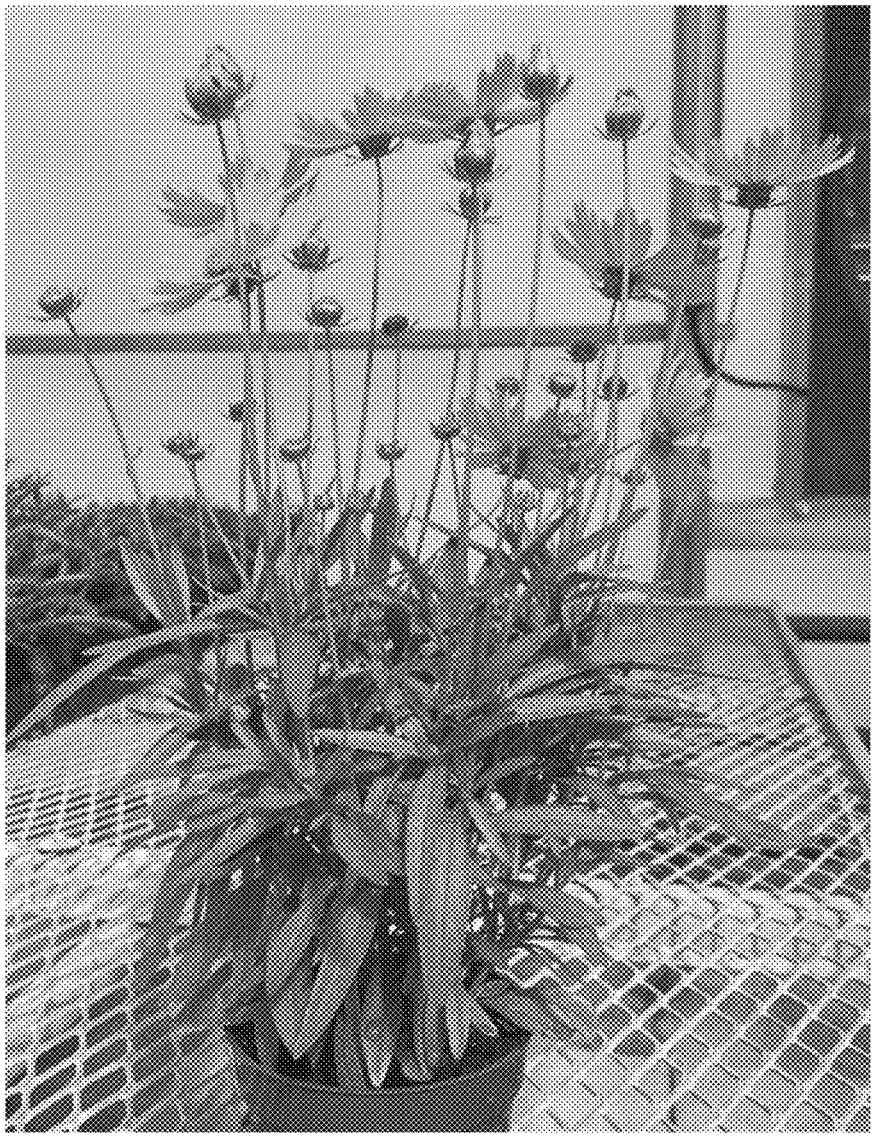

Botanical designation: *Coreopsis hybrida.*
Cultivar denomination: 'BALUPTOLD'.

BACKGROUND OF THE INVENTION

The present invention relates to a new and distinct cultivar of *Coreopsis* plant, commonly referred to as Tickseed, botanically known as *Coreopsis hybrida*, and hereinafter referred to by the name 'Baluptold'.

The new *Coreopsis* plant is a naturally-occurring whole plant mutation of *Coreopsis hybrida* 'Baluptgonz', disclosed in U.S. Plant Pat. No. 28,882. The new *Coreopsis* plant was discovered and selected by the Inventor as a single flowering plant from within a population of plants of 'Baluptgonz' in a controlled environment in Castalia, Ohio on Jun. 22, 2021.

Asexual reproduction of the new *Coreopsis* plant by vegetative cuttings in controlled environments in Castalia, Ohio and West Chicago, Illinois since June 2021 has shown that the unique features of this new *Coreopsis* plant are stable and reproduced true to type in successive generations.

SUMMARY OF THE INVENTION

Plants of the new *Coreopsis* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Baluptold'. These characteristics in combination distinguish 'Baluptold' as a new and distinct cultivar of *Coreopsis* plant:

1. Upright and mounded plant habit.
2. Moderately vigorous growth habit.

3. Freely branching habit.
4. Medium green-colored leaves.
5. Freely flowering habit with numerous inflorescences per plant.
6. Single-type daisy inflorescences with bright yellow-colored ray florets.
7. Good garden performance.

Plants of the new *Coreopsis* differ primarily from plants of the mutation parent, 'Baluptgonz' in ray floret color as ray florets of inflorescences of plants of the new *Coreopsis* are bright yellow in color whereas ray florets of inflorescences of plants of 'Baluptgonz' are medium golden yellow and orange red bi-colored. In addition, plants of the new *Coreopsis* are not as vigorous as plants of 'Baluptgonz'.

Plants of the new *Coreopsis* can be compared to *Coreopsis hybrida* 'Baluptowed', disclosed in U.S. Plant Pat. No. 28,865. Plants of the new *Coreopsis* differ primarily from plants of 'Baluptowed' in ray floret color as ray florets of inflorescences of plants of the new *Coreopsis* are bright yellow in color whereas ray florets of inflorescences of plants of 'Baluptowed' are yellow and burgundy red bi-colored. In addition, inflorescences of plants of the new *Coreopsis* have fewer ray florets than inflorescences of plants of 'Baluptowed'.

BRIEF DESCRIPTION OF THE PHOTOGRAPHS

The accompanying photographs illustrate the overall appearance of the new *Coreopsis* plant. The photographs show the colors as true as it is reasonably possible to obtain in colored reproductions of this type. Colors in the photographs may differ slightly from the color values cited in the detailed botanical description which accurately describe the colors of the new *Coreopsis* plant.

The photograph on the first sheet (FIG. 1) comprises a side perspective view of a typical flowering plant of 'Baluptold' grown in a container.

Figure 2:
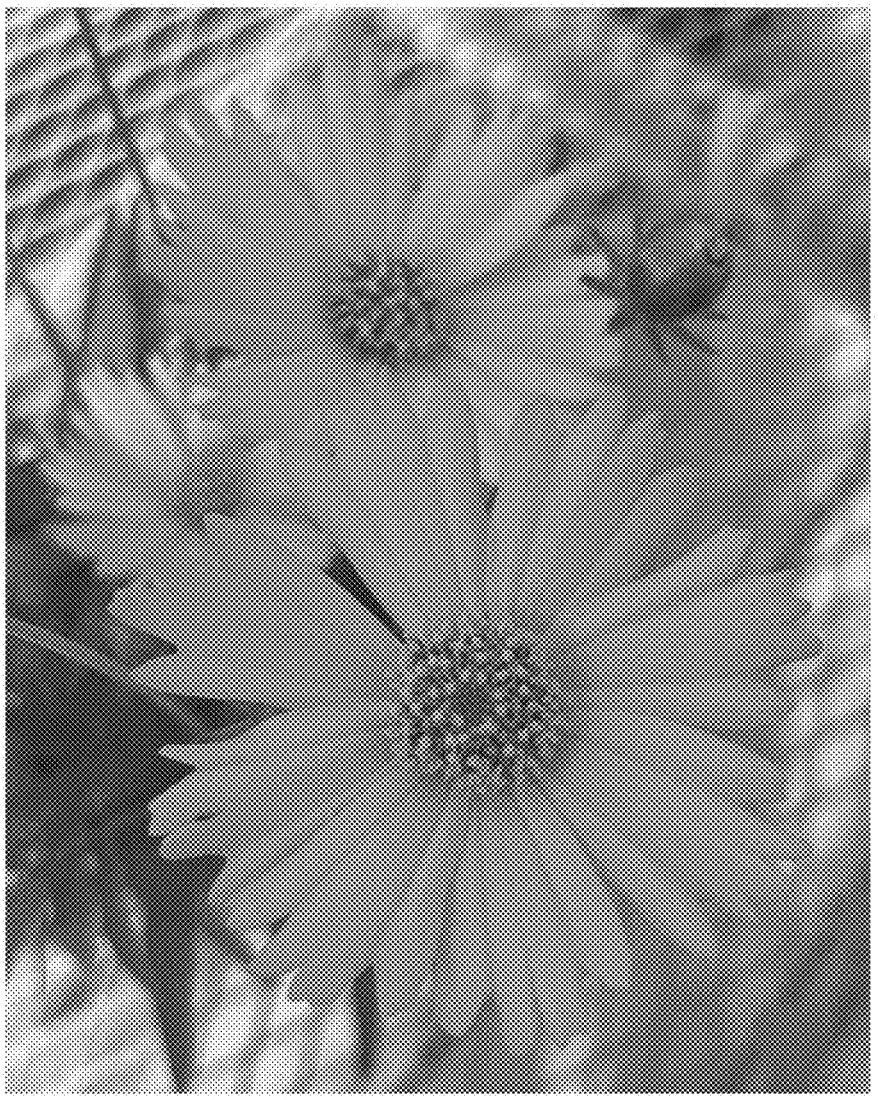

The photograph on the second sheet (FIG. 2) is a close-up view of a typical flowering plant of 'Baluptold'.

DETAILED BOTANICAL DESCRIPTION

The aforementioned photographs and following observations and measurements describe plants grown in 10-cm containers in a polyethylene-covered greenhouse in West Chicago, Illinois during the late winter and early spring and under cultural practices similar to those used in commercial *Coreopsis* plant production. During the production of the plants, day temperatures averaged 25° C. and night temperatures averaged 10° C. Plants were pinched twice and were twelve weeks old when the photographs and description were taken. In the following description, color references are made to The Royal Horticultural Society Colour Chart, Sixth Edition, except where general terms of ordinary dictionary significance are used. Measurements represent averages for typical flowering plants.

Botanical classification: *Coreopsis hybrida* 'Baluptold'.

Parentage: Naturally-occurring whole plant mutation of *Coreopsis hybrida* 'Baluptgonz', disclosed in U.S. Plant Pat. No. 28,882.

Propagation:

*Type*.—By vegetative terminal stem cuttings.

*Time to initiate roots*.—About ten to twelve days at temperatures about 21° C.

*Time to produce a rooted young plant*.—About five to six weeks at temperatures about 21° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright and mounding plant habit; columnar in overall plant shape; freely branching habit with about seven to eight primary lateral branches each with secondary lateral branches potentially developing at every node; moderately vigorous growth habit and moderate growth rate.

*Plant height, soil level to top of foliar plane*.—About 14 cm to 15 cm.

*Plant height, soil level to top of floral plane*.—About 27 cm to 29 cm.

*Plant diameter or spread*.—About 19 cm to 23 cm.

*Lateral branches*.—Length: About 9 cm to 12 cm. Diameter: About 3 mm to 4 mm. Internode length: About 3 cm to 3.2 cm. Aspect: Upright to about 20° from vertical. Strength: Strong, not flexible. Texture and luster: Pubescent; slightly glossy. Color: Close to 144A.

Leaf description:

*Arrangement*.—Opposite, simple.

*Length*.—About 5 cm to 5.2 cm.

*Width*.—About 1.1 cm to 1.3 cm.

*Shape*.—Linear; leaves occasionally with one to two proximal lobes.

*Apex*.—Acute.

*Base*.—Attenuate to cuneate.

*Margin*.—Entire or proximally one to two-lobed; lobes are deep and divergent.

*Texture and luster, upper and lower surfaces*.—Pubescent; semi-glossy.

*Venation pattern*.—Pinnate.

*Color*.—Developing leaves, upper and lower surfaces: Close to 146A. Fully expanded leaves, upper surface: Close to 146A; venation, close to 146B. Fully expanded leaves, lower surface: Close to 146B; venation, close to 146A to 146B.

*Petioles*.—Length: About 1.5 cm to 1.8 cm. Width: About 1 mm to 1.5 mm. Texture and luster: Pubescent; semi-glossy. Color, upper and lower surfaces: Close to 144A.

Inflorescence description:

*Appearance*.—Single-type daisy terminal and axillary inflorescences with ray and disc florets arranged acropetally on a capitulum; inflorescences positioned above and beyond the foliar plane on strong peduncles; inflorescences face upright.

*Flowering habit*.—Freely flowering habit; about 35 to 40 inflorescences developing per plant at one time; flowering continuous during the flowering season.

*Fragrance*.—Faintly fragrant; pleasant.

*Time to flower*.—Depending on temperature, plants begin flowering about ten to twelve weeks after planting rooted young plants.

*Post-production longevity*.—Depending on temperature, inflorescences maintain good substance for about one to three weeks on the plant; inflorescences persistent.

*Inflorescence buds*.—Height: About 4 mm. Diameter: About 6 mm. Shape: Oblate. Texture and luster: Smooth, glabrous; glossy. Color: Close to 147A.

*Inflorescence size*.—Diameter: About 7 cm. Depth (height): About 4.5 cm. Disc diameter: About 6 mm to 9 mm. Receptacle height: About 4 mm. Receptacle diameter: About 4 mm. Receptacle color: Close to 144A.

*Ray florets*.—Quantity and arrangement: About 32 to 35 arranged in a single whorl. Length: About 3.5 cm to 3.7 cm. Width: About 1.5 cm to 2 cm. Shape: Linear. Apex: Obtuse, emarginate or praemorse; ragged appearance. Base: Acuminate. Margin: Entire; not undulate. Texture and luster, upper and lower surfaces: Smooth, glabrous; matte. Color: When opening, upper and lower surfaces: Close to 14A. Fully developed, upper surface: Close to 14A; venation, close to 14A; color does not change with subsequent development. Fully developed, lower surface: Close to 14B to 14C; venation, close to 14B to 14C; color does not change with subsequent development.

*Disc florets*.—Quantity and arrangement: About 35 to 40 arranged in about three to four whorls. Shape: Tubular, slender; apex dentate. Length: About 1 cm. Diameter: About 4.5 mm. Texture and luster: Smooth, glabrous; matte. Color, immature and mature: Close to 17A; color does not change with subsequent development.

*Phyllaries, inner whorl*.—Quantity and arrangement: About eight in a single whorl; fused at the base. Length: About 9 mm. Width: About 5 mm. Shape: Deltoid. Apex: Acuminate. Margin: Entire. Texture and luster, upper and lower surfaces: Smooth, glabrous; waxy; semi-glossy. Color, upper and lower surfaces: Close to 152A.

*Phyllaries, outer whorl*.—Quantity and arrangement: About seven to eight in a single whorl; fused at the base. Length: About 7 mm. Width: About 3 mm. Shape: Linear. Apex: Acuminate. Margin: Entire. Texture and luster, upper and lower surfaces: Smooth, glabrous; waxy; semi-glossy. Color, upper and lower surfaces: Close to 144A.

*Peduncles*.—Length: About 15 cm to 17.5 cm. Diameter: About 2 mm to 2.25 mm. Strength: Strong, wiry and somewhat flexible. Aspect: Mostly upright. Texture and luster: Smooth, glabrous; glossy. Color: Close to 144A.

*Reproductive organs*.—Androecium (present on disc florets only): Quantity per disc floret: Five. Filament length: About 1 mm. Filament color: Close to 7A. Anther shape: Lanceolate. Anther size: About 2.5 mm by 0.5 mm. Anther color: Close to 162A. Pollen amount: Moderate. Pollen color: Close to 17A. Gynoecium (present on disc florets only): Quantity per floret: One. Pistil length: About 7 mm. Stigma diameter: About 1.5 mm. Stigma shape: Tri-parted. Stigma color: Close to 17A. Style length: About 6 mm. Style color: Close to 5A. Ovary color: Close to N144A.

*Seeds and fruits*.—To date, seed and fruit production has not been observed on plants of the new *Coreopsis*.

Pathogen & pest resistance: To date, plants of the new *Coreopsis* have not been shown to be resistant to pathogens and pests common to *Coreopsis* plants.

Garden performance: Plants of the new *Coreopsis* have exhibited good tolerance to rain, wind and are hardy to USDA Hardiness Zone 5a.

It is claimed:

1. A new and distinct *Coreopsis* plant named 'Baluptold' as herein illustrated and described.

* * * * *